United States Patent [19]

Geria

[11] Patent Number: 5,562,908
[45] Date of Patent: Oct. 8, 1996

[54] TREATMENT OF SINUS HEADACHE

[75] Inventor: Navin M. Geria, Warren, N.J.

[73] Assignee: Warner-Lambert Company, Morris Plains, N.J.

[21] Appl. No.: 238,124

[22] Filed: Jul. 1, 1994

Related U.S. Application Data

[63] Continuation of Ser. No. 500,610, Mar. 27, 1990.

[51] Int. Cl.⁶ .................................................. A61F 13/00
[52] U.S. Cl. ............................................. 424/434; 424/435
[58] Field of Search .................................. 424/434, 435; 514/474

[56]  References Cited

U.S. PATENT DOCUMENTS

| | | | |
|---|---|---|---|
| 2,868,689 | 1/1959 | Florestano et al. | 167/52 |
| 3,832,259 | 8/1974 | Berkeley | 424/45 |
| 4,466,973 | 8/1984 | Rennie | 424/267 |
| 4,808,410 | 2/1989 | Sorrentino et al. | 424/435 |
| 4,940,728 | 7/1990 | Postley | 514/474 |

OTHER PUBLICATIONS

Chemical Abstracts, vol. 110, No. 25, Jun. 19, 1989, p. 46, Abstract No. 2253045.

*Primary Examiner*—Thurman K. Page
*Assistant Examiner*—William E. Benston, Jr.
*Attorney, Agent, or Firm*—Jean B. Barish

[57]  ABSTRACT

The present invention contemplates nasal compositions effective for relieving mammalian sinus headache associated with inflamed or congested turbinates, or both, accompanied by localized pain perceived on the septum, containing an anaesthetically effective amount of a non-addictive, rapidly absorbable anaesthetic component such anaesthetic being the sole active ingredient in the composition or being combined with a decongestant of the sympathomimetic amine class.

2 Claims, No Drawings

TREATMENT OF SINUS HEADACHE

This is a continuation of prior application Ser. No. 07/500,610 filed on Mar. 27, 1990 pending.

FIELD OF INVENTION

This invention relates to the treatment of sinus headache encountered in mammals suffering from congestion of the sinuses. More particularly, the invention relates to compounds, compositions and methods useful in alleviating the pain associated with sinusidal irritation or blockage.

BACKGROUND OF THE INVENTION

Sinus headache is a clinical manifestation of pain caused by an underlying mucosal inflammation and/or engorgement of the turbinates, ostia, nasofrontal ducts or superior nasal spaces. In infection or blockage of paranasal sinuses, accompanied by pain over the antrum or in the forehead, the mechanism of pain involves changes in pressure and irritation of pain-sensitive sinus walls especially the mucosa covering the approaches to the paranasal sinuses (Harrison's PRINCIPLES OF INTERNAL MEDICINE, Isselbacher et al, 9th Ed., 1980, McGraw-Hill Book Co.).

A remarkable property of sinus pain is that it tends to recur and subside at the same hours. Typically, the headache commences in the morning (frontal) or early afternoon (maxillary) and subsides in the early or late evening. The pain is dull and aching, and is made worse by changing head position (Cecil, TEXTBOOK OF MEDICINE, vol 2, Wyngaarden & Smith, 16th Ed., 1982, W. B. Saunders & Co.). It occurs on awakening, with gradual disappearance when the person is upright, and returning later in the day. The morning pain is believed to be due to the sinuses filling during the night and emptying on arising after an erect posture has been assumed. Stooping also intensifies the pain by pressure change, as do blowing the nose and jarring the head. Some (Wyngaarden et al) believe that most of the discomfort comes from the ostia, which are many times more sensitive than the relatively insensitive walls of the sinuses. Others (Isselbacher et al) recognize the proposition that the orifice of the sinus may be the source, but suggest that it is more likely that the pain arises in the sensitive mucous membrane of the sinus. It may persist after all purulent secretions have disappeared because of the mechanism of blockage of the orifice by boggy membranes and a vacuum or suction effect on the sinus wall.

During air flights, sinus headache, including that without a history of inflammation, tends to occur on descent, when the relative pressure on the blocked viscus falls.

From the neurological standpoint, narrowed nasal passages caused by inflammatory or allergic turbinate swelling are responsible not only for direct nerve irritations felt along the route originating from the nasociliary and anterior and posterior ethmoidal branches of the ophthalmic division of the trigeminal (fifth cranial) nerve, but also for the closure of the sinus ostia, with retention of normal mucous or of eventual inflammatory exudates. Headaches arising from such retention are referred, inter alia, to the frontal sinuses (above the eyes, to the vertex and temples), to the anterior ethmoids (pressure between the eyes) and to the temples (DISEASES OF THE NOSE, THROAT, AND EAR, Jackson et al, 2nd Ed., 1959, Saunders).

One method for relieving the pain associated with sinus headache is the application of cocaine to the nasal mucosa. This well-known drug, a naturally occurring alkaloid (ecgonine methyl ester benzoate) produces excellent surface anaesthesia and intense vasoconstriction when applied to mucous surfaces such as those in the nose and throat. Indeed, its vasoconstrictive action is so severe that combining it with a vasoconstrictor such as epinephrine is not only unnecessary because it does not delay absorption, but because it may also increase the likelihood of arrhythmias and ventricular fibrillation. For example, the moistening of dry cocaine powder with epinephrine solution to form a so-called "cocaine mud" for use on the nasal mucosa is particularly dangerous (AMA DRUG EVALUATIONS, 4TH Ed., 1980, p. 295).

Notwithstanding its usefulness as a local anaesthetic, cocaine is known to suffer from several disadvantages. It is the prototype of a drug that in high doses produces euphoric excitement and hallucinatory experiences. These properties are highly esteemed by experienced drug users and lead to some degree of psychic dependence. (THE MERCK MANUAL, 14th Ed., 1982, p. 1427). Cocaine is the best example of a drug to which neither tolerance nor physical dependence develops, but to which psychic dependence develops that can lead to addiction. The tendency to continue taking the drug is strong. When inhaled, cocaine produces a condition of hyperstimulation, alertness, euphoria, and feelings of great power. The excitation and "high" are similar to that produced by injection of high doses of amphetamine. With repetition, toxic effects such as tachycardia, hypertension, mydriasis, muscle-twitching, formication ("cocaine bugs") miniaturized visual hallucinations, sleeplessness and extreme nervousness appear. Stimulation is followed by depression and, finally, by death from ventilatory depression. (AMA DRUG EVALUATIONS, p. 296). Due to its psychic dependence and tolerance, the drug is classified under Schedule II of the Controlled Substances Act.

Procaine, another compound long-recognized for its anaesthetic properties, has been suggested for application to inflamed nasal mucous membranes, the turbinates or about the ostium of the frontal nasal duct to eliminate the headache that stems from the nose and 'sinus disease' (WOLFF's HEADACHE AND OTHER HEAD PAIN, 4th Ed., 1980, Oxford University Press, p.624). This suggestion notwithstanding, others (AMA DRUG EVALUATIONS, p. 304) state that procaine is not useful for topical applications, most likely because it is not quickly absorbed from mucous surfaces, which limits its utility as a local anaesthetic. Procaine when "snorted" viz., inhaled, produces a local sensation not unlike cocaine and may even produce some "high". (THE MERCK MANUAL, p. 1428).

Dyclonine is a local anaesthetic known to be useful for relieving surface pain and itching due to minor burns or trauma, surgical wounds, pruritus ani or vulvae, insect bites, and pruritic dermatoses. Inflamed or broken skin surfaces are particularly amenable to treatment with dyclonine (Tech. Bull., Ganes Chemicals, Inc., New York, N.Y.). The drug may be used to anaesthetize mucous membranes prior to endoscopy; to remove the pain of minor burns and gynecologic or proctologic procedures and in the eye, where it does not produce miosis or mydriasis.

Dyclonine [1-(4-Butoxyphenyl)-3-(1-piperidinyl)-1-propanone] is, in the form of its hydrochloride salt, a white crystalline powder; soluble in water, acetone and alcohol; and stable for a minimum of 12 months when stored in an airtight container at room temperature. (THE MERCK INDEX, 10th Ed., 1983, p. 3451). Unlike most other local anaesthetic agents, dyclonine hydrochloride is a ketone. Its molecular structure does not involve the usual ester or amide linkages of procaine-type local anaesthetics.

Dyclonine is shown in U.S. Pat. No. 2,771,391 as being useful in 0.1 to 5.0 percent concentrations as a local and epidural anaesthetic.

Therapeutic compositions useful in the treatment of intra-articular and intra-muscular discomfort comprising from about 0.005 to about 0.10 parts by weight of a glucocorticoidal agent and from about 0.25 to about 0.75 parts by weight of a topical anaesthetic compound such dyclonine hydrochloride are shown in U.S. Pat. No. 4,312,865.

Combinations of phenol and dyclonine hydrochloride, the latter in concentrations of from 0.05 to 2.0 w/v percent, are disclosed in U.S. Pat. No. 4,808,410 for eliciting a topical anaesthetic and antimicrobial response for oral health care purposes.

Another anaesthetic agent known to be useful when applied topically to the skin or mucous membranes is pramoxine {4-[3-(4-butoxyphenoxy)propyl]morpholine}, (THE MERCK INDEX, 10th Ed., p. 7603; AMA DRUG EVALUATIONS, 4th Ed., p. 302). Pramoxine is derived from morpholine and, like dyclonine, is chemically different from ester- or amide-type anaesthetics. When applied topically to the skin or mucous membranes, it relieves pain caused by minor burns and wounds and pruritus secondary to dermatoses or hemorrhoids. It facilitates sigmoidoscopic examinations and exerts anaesthetic action on laryngopharyngeal surfaces prior to endotracheal intubation. For these purposes it is used in the form of a cream or jelly in 1% concentration.

Belgian Patent No. 776,769 shows prolonged-action anaesthetic compositions of saxitoxin, an extract of *Saxidonous giganteus,* and various anaesthetics such as procaine, cocaine and pramoxine.

PCT Priority Application Number 070,904, teaches pharmaceutical compositions comprising disaccharide polysulfate-aluminum compounds and local anaesthetics such as pramoxine, dyclonine etc., for alleviating symptoms caused by hemorrhoids and in wound healing.

Another approach to the treatment of sinus headache is the use of drugs which mimic the effects of stimulation of the sympathetic division of the autonomic nervous system which consists of neurons, ganglia and plexuses that innervate and regulate the heart, blood vessels and visceral smooth muscles. These drugs are known and classified as 'sympathomimetics' or 'adrenergics' because they act either directly to stimulate adrenergic receptors (alpha, beta), or indirectly by releasing norepinephrine from its storage site in the adrenergic nerve endings (AMA DRUG EVALUATIONS, p 451; THE MERCK MANUAL, 14th Ed., 1982, pp 2344 et seq.). The terms "sympathomimetic" and "adrenergic" are used herein interchangeably. The sympathomimetics are also known as "decongestants".

The other of the two divisions of the autonomic nervous system is the 'parasympathetic', which produces responses opposite to those evoked by the sympathetic system. The proper balance between sympathetic and parasympathetic efferent impulses affects the vasomotor integrity of the nasal mucosa. Activation of the parasympathetic division of the autonomic nervous system produces vasodilatation and increases secretion. Activation of the sympathetic division produces vasoconstriction and decreases secretion.

Stimulation of the alpha (excitatory) adrenergic receptors of vascular smooth muscle by adrenergic drugs, results in the constriction of dilated arterioles within the nasal mucosa, reduction of blood flow in the engorged, edematous area and nasal decongestion. Opening of obstructed nasal passages improves nasal ventilation and aeration, and drainage of the sinuses, thus relieving headache of sinus origin (AMA DRUG EVALUATIONS, Ibid).

Adrenergic agents commonly used for relief of nasal congestion are the aryl alkyl amines such as phenylephrine, epinephrine, ephedrine, desoxyphedrine, phenylpropanolamine and tuaminoheptane; the imidazolines such as naphazoline, oxymetazoline, tetrahydrozoline and xylometazoline; and cyclo alkyl amines such as propylhexadrine (DRUG FACTS & COMPARISONS, J. B. Lipincott Co. 1989; HANDBOOK OF NONPRESCRIPTION DRUGS, 8th Ed., 1986, American Pharmaceutical Association). These sympathomimetic amines are known to cause marked vasoconstriction when applied to nasal and pharyngeal mucosal surfaces. They are useful in relieving mucosal congestion accompanying hay fever, allergic rhinitis, acute coryza, sinusitis and other respiratory conditions.

The use of imidazolines for reducing the swelling of mucous membranes of the nose is disclosed in U.S. Pat. No. 3,147,275.

Combinations of tricyclic anti-depressants with various sympathomimetic vasoconstrictors such as oxymetazoline, phenylephrine etc. for preventing and treating irritation of the mucous membranes of the nose are disclosed in U.S. Pat. No. 4,603,131.

Combinations of cromolyn and oxymetazoline for use in the nose are shown in U.S. Pat. Nos. 3,975,536 and 3,975,536.

Prior art commercially available formulations containing sympathomimetics such as phenylephrine, naphazoline, oxymetazoline, xylometazoline and tetrahydrozoline in nasal sprays and nose drops are shown in PHYSICIAN'S DESK REFERENCE, 1989 and HANDBOOK OF NONPRESCRIPTION DRUGS, 8th Edition (supra).

In view of the foregoing, it is clear that a need exists for topically applicable nasal compositions which are capable of eliciting a therapeutic response in the mucous membranes of the sinuses of mammals; which exert a rapid onset of anaesthetic action and duration of effect comparable to that of cocaine or procaine without their attendant side effects and disadvantages and, when combined with appropriate adrenergics impart a prompt, highly effective, concomitant decongestive action on the nasal sinuses.

SUMMARY OF THE INVENTION

The present invention contemplates nasal compositions effective for relieving mammalian sinus headache associated with inflamed or congested turbinates, or both, accompanied by localized pain perceived on the septum, containing an anaesthetically effective amount of a non-addictive, rapidly absorbable anaesthetic component such anaesthetic being the sole active ingredient in the composition or being combined with a decongestant of the sympathomimetic amine class.

More particularly, the preferred embodiment of this invention provides compositions useful for the symptomatic relief of sinus headache and nasal congestion comprising anaesthetically effective amounts of dyclonine or pramoxine in the form of an addition salt with a physiologically tolerable (pharmacologically acceptable) acid, preferably in combination with an adrenergically effective amount of a sympathomimetic amine, incorporated in a pharmaceutically acceptable carrier.

Further, this invention provides methods for relieving symptoms of sinusidal pain associated with coryza, nasal congestion, allergic rhinitis and sinusitis by the direct application to affected nasal mucosa of an anaesthetically effective amount of a dyclonine or pramoxine acid addition salt alone or in combination with an adrenergic decongestant incorporated in a pharmaceutically acceptable carrier.

DETAILED DESCRIPTION OF THE INVENTION

Although, as noted above, local anaesthetics such as dyclonine and pramoxine have been used topically on the skin and locally on mucosal tissues of the mouth, larynx, trachea and esophagus and in urologic endoscopy, gynecology and proctology, the prior art has not recognized the utility of these compounds in anaesthetically effective concentrations in the form of pharmaceutically acceptable compositions for direct application to mucosal membranes of the sinuses to relieve headache and congestion, preferably in combination with an effective amount of a sympathomimetic amine decongestant.

Further, although the prior art teaches the local application of cocaine to sinusidal tissues, the use of this drug for this purpose is contraindicated because of its addictive properties and susceptibility to abuse as well as its toxicity.

I have now discovered that compositions containing dyclonine or pramoxine as the active, non-addictive, rapidly absorbing, anaesthetic ingredient in a concentration from about 0.01 percent weight/weight to about 0.1 percent weight/weight, preferably in an amount from about 0.025 percent weight/weight to about 0.075 percent weight/weight, incorporated in a pharmaceutically acceptable vehicle, as the sole therapeutic ingredient or, preferably, in combination with a decongestant for example a sympathomimetic amine such as an arylalkylamine, imidazoline or cycloalkylamine in a concentration from about 0.1 percent weight/weight to about 1.0 percent weight/weight, preferably from about 0.25 percent to about 0.75 percent weight/weight are surprisingly effective in the treatment of sinus headache.

Sympathomimetic amine decongestants useful in the present invention may be selected from the group consisting of arylalkylamines such as phenylephrine, epinephrine, ephedrine, desoxyphedrine, phenylpropanolamine and tuaminoheptane; the imidazolines such as naphazoline, oxymetazoline, tetrahydrozoline and xylometazoline; and cyclo alkylamines such as propylhexadrine and mixtures thereof.

Although the precise mechanism of action of the novel compositions of this invention is not fully known, I believe that the rapid onset of action and quick relief of headache associated with sinusidal pain, particularly when accompanied by inflammation and/or congestion, following application of the novel compositions, is attributable to a synergistic coaction between the anaesthetic and decongestant components. When the mucosal tissues of the sinuses block the sinus openings by expansion, the resulting pressure causes headache pain. Relief is obtained by local application of the anaesthetic and removal of the cause of the congestion. The quick and effective elimination of this duality of underlying causes is achievable when the anaesthetic/decongestant combination is applied directly to the affected area.

The compositions of the present invention may be administered directly to the nasal sinuses in the form of a nasal spray, nasal gel, nose drops or insufflation.

As noted above, the anaesthetic and decongestant components of the compositions of this invention are suitably formulated as pharmacologically acceptable acid addition salts. By the term "pharmacologically acceptable acid addition salts" is meant any non-toxic pharmaceutically suitable salt of a compound described above which has the desired pharmacologic properties in mammals. Preparation of such salts is well known to those skilled in pharmaceutical science. Pharmacologically acceptable acid addition salts of the above compounds include, but are not limited to, the hydrochloride, hydrobromide, hydroiodide, sulfate, bisulfate, nitrate, citrate, tartrate, bitartrate, lactate, phosphate, maleate, malate, fumarate, succinate, acetate and pamoate.

Suitable non-toxic pharmaceutically acceptable carriers for the anaesthetics and decongestants of this invention for the purpose of delivering the active components to the site of action will be apparent to those skilled in the art of pharmaceutical compounding. For this purpose reference is made to the text entitled 'REMINGTON'S PHARMACEUTICAL SCIENCES', 14TH Ed., 1970. Obviously the choice of suitable carriers will depend on the exact nature of the particular nasal dosage form desired, that is to say, whether the drugs are to be formulated into a nasal solution, for use as a spray or as drops; a nasal suspension; nasal gel or an insufflation. Preferred nasal dosage forms are nasal sprays and drops which contain a major amount of water, suitably purified. Minor amounts of other ingredients such as pH adjusters, emulsifiers, flavoring agents such as menthol and eucalyptol, wetting agents such as thonzonium bromide (THE MERCK INDEX, 10th Ed., p. 9221) and surfactants such as polysorbate (Ibid. p. 7458) may also be present. Most preferably, the nasal composition is isotonic. i.e., it has the same osmotic pressure as blood serum. As is well known in the pharmaceutical art, isotonicity is accomplished by the addition of suitable quantities of salts. Sodium chloride is the preferred salt.

Examples of suitable preservatives for inclusion in the compositions of this invention are benzalkonium chloride, edetate disodium, sodium bisulfite, phenylmercuric acetate, cetylpyridinium chloride, thimerosal, chlorobutanol, cetyltrimethyl ammonium bromide, methylparaben, propylparaben and butylparaben.

As buffers, suitable examples include dibasic sodium phosphate, monobasic sodium phosphate, citric acid, sodium citrate, acetic acid, sodium acetate, boric acid, sodium carbonate, sodium borate, hydrochloric acid and sodium hydroxide.

Examples of the preparation of typical nasal compositions containing the therapeutically active components of this invention are set forth below. It is to be understood that these examples are given by way of illustration only and are not to be construed as limiting the invention either in spirit or in scope, as many modifications both in materials and in methods will be apparent to those skilled in the art.

EXAMPLE 1

| | % W/W |
|---|---|
| Thonzonium Bromide | 0.05 |
| Oxymetazoline Hydrochloride | 0.05 |
| Dyclonine Hydrochloride | 0.50 |
| Sodium Phosphate, Monobasic, Crystal | 1.10 |
| Sodium Phosphate, Dibasic, Anhydrous | 0.30 |
| Thimerosal NF | 0.002 |
| Methyl Paraben USP | 0.0065 |
| Propyl Paraben USP | 0.0035 |
| Menthol USP | 0.10 |
| Eucalyptol NF | 0.02 |
| Camphor USP | 0.02 |

EXAMPLE 1

| | % W/W |
|---|---|
| Ethyl Alcohol USP | 0.06 |
| Cetylpyridinium Chloride | 0.05 |
| Sodium Chloride Reagent | 0.20 |
| Polysorbate 80 | 0.50 |
| Purified Water q.s. | 100.00 |

Oxymetazoline hydrochloride, dyclonine hydrochloride and cetylpyridinium chloride are dissolved in 95 ml of purified water at 25°–30° C. with mixing to form a clear solution. The menthol, camphor, eucalyptol and alcohol are separately mixed to form a eutectic mixture in which are dissolved with mixing methyl paraben and propyl paraben. Polysorbate 80 is added and, after mixing, the resulting composition is added with stirring to the previously prepared aqueous solution of active ingredients, the transfer being aided with a small quantity of water. The monobasic and dibasic sodium phosphates, thimerosal and sodium chloride are dissolved therein, the resultant composition is brought to volume with purified water at 25° C. batch temperature and filtered thru a 0.22 mm filter.

EXAMPLE 2

| | % W/W |
|---|---|
| Thonzonium Bromide | 0.05 |
| Dyclonine Hydrochloride | 0.50 |
| Sodium Phosphate, Monobasic, Crystal | 1.10 |
| Sodium Phosphate, Dibasic, Anhydrous | 0.30 |
| Thimerosal NF | 0.002 |
| Methyl Paraben USP | 0.0065 |
| Propyl Paraben USP | 0.0035 |
| Menthol USP | 0.1000 |
| Eucalyptol NF | 0.02 |
| Camphor USP | 0.02 |
| Ethyl Alcohol USP | 0.06 |
| Cetylpyridinium Chloride NF | 0.05 |
| Sodium Chloride Reagent | 0.20 |
| Polysorbate 80 | 0.50 |
| Purified Water q.s. | 100.00 |

Dyclonine hydrochloride and cetylpyridinium chloride are dissolved in 95 ml of water at a temperature of 25°–30° C. with mixing. Separately, a eutectic mixture is formed with menthol, eucalyptol, camphor and alcohol in which are dissolved with mixing methyl paraben, propyl paraben and thonzonium bromide. Polysorbate 80 is added thereto with mixing and the resultant composition is added to the previously prepared aqueous solution of dyclonine hydrochloride and cetylpyridinium chloride with the aid of a small quantity of water. To this are added and dissolved the monobasic and dibasic sodium phosphates, thiomersal and sodium chloride. The mixture is brought up to volume with water at batch temperature and filtered through a 0.22 mm filter.

EXAMPLE 3

| | % W/W |
|---|---|
| Thonzonium Bromide | 0.05 |
| Dyclonine Hydrochloride | 1.00 |
| Sodium Phosphate, Monobasic, Crystal | 1.10 |
| Sodium Phosphate, Dibasic, Anhydrous | 0.30 |
| Thimerosal NF | 0.002 |
| Methyl Paraben USP | 0.0065 |
| Propyl Paraben USP | 0.0035 |
| Menthol USP | 0.1000 |
| Eucalyptol NF | 0.02 |
| Camphor USP | 0.02 |
| Ethyl Alcohol USP | 0.06 |
| Cetylpyridinium Chloride NF | 0.05 |
| Sodium Chloride Reagent | 0.20 |
| Polysorbate 80 | 0.50 |
| Purified Water q.s. | 100.00 |

Dyclonine hydrochloride and cetylpyridinium chloride are dissolved in 95 ml of water at a temperature of 25°–30° C. with mixing. Separately, a eutectic mixture is formed with menthol, eucalyptol, camphor and alcohol in which are dissolved with mixing methyl paraben, propyl paraben and thonzonium bromide. Polysorbate 80 is added thereto with mixing and the resultant composition is added to the previously prepared aqueous solution of dyclonine hydrochloride and cetylpyridinium chloride with the aid of a small quantity of water. To this are added and dissolved the monobasic and dibasic sodium phosphates, thimerosal and sodium chloride. The mixture is brought to volume with water at batch temperature and filtered through a 0.22 mm filter.

The present invention has been described generally and with respect to preferred embodiments. It will be clear to those skilled in the art that modifications and/or variations of the disclosed compositions can be made without departing from the scope of the invention set forth herein. The invention is defined by the claims which follow.

I claim:

1. A topically applicable nasal composition which elicits a therapeutic response in the mucous membranes of the sinuses of a mammal comprising an anesthetically effective amount for relieving mammalian sinus headache of an acid addition salt of dyclonine or pramoxine.

2. A composition according to claim 1 wherein the pharmaceutically acceptable carrier is selected from the group consisting of a nasal spray, nasal gel, nose drops and an insufflation.

\* \* \* \* \*